United States Patent
McDonnall et al.

(10) Patent No.: US 11,272,956 B2
(45) Date of Patent: Mar. 15, 2022

(54) SYSTEMS AND METHODS FOR IMPLANTING ELECTRODE LEADS

(71) Applicant: Ripple, LLC, Salt Lake City, UT (US)

(72) Inventors: Daniel Allen McDonnall, Salt Lake City, UT (US); Nathaniel Anthony Srok, Salt Lake City, UT (US); Christopher Farand Smith, North Salt Lake, UT (US)

(*) Notice: Subject to any disclaimer, the term of this patent is extended or adjusted under 35 U.S.C. 154(b) by 273 days.

(21) Appl. No.: 16/355,804

(22) Filed: Mar. 17, 2019

(65) Prior Publication Data

US 2020/0289155 A1    Sep. 17, 2020

(51) Int. Cl.
| | |
|---|---|
| A61B 17/34 | (2006.01) |
| A61N 1/05 | (2006.01) |
| A61B 17/00 | (2006.01) |
| A61F 2/72 | (2006.01) |

(52) U.S. Cl.
CPC ...... *A61B 17/3468* (2013.01); *A61B 17/3421* (2013.01); *A61N 1/05* (2013.01); *A61B 2017/00367* (2013.01); *A61B 2017/00438* (2013.01); *A61F 2/72* (2013.01)

(58) Field of Classification Search
CPC . A61B 17/3468; A61B 17/34; A61B 17/3417; A61B 17/3421; A61B 2017/3433; A61B 17/3439; A61B 2017/3443; A61B 2017/3445; A61B 2017/3447; A61B 2017/3449; A61B 17/3462; A61B 2017/00367; A61B 2017/00389; A61B 2017/0042; A61B 2017/00429; A61B 2017/00433; A61B 2017/00438; A61N 1/05; A61N 1/0502; A61N 1/0504
See application file for complete search history.

(56) References Cited

U.S. PATENT DOCUMENTS

| | | | | |
|---|---|---|---|---|
| 7,993,356 B2* | 8/2011 | Rapacki | ............ | A61B 17/3468 606/153 |
| 8,968,331 B1* | 3/2015 | Sochor | ............... | A61B 17/3468 606/129 |
| 2002/0107482 A1* | 8/2002 | Rocamora | .......... | A61B 17/3439 604/161 |
| 2002/0161424 A1* | 10/2002 | Rapacki | ............. | A61B 17/3468 623/1.1 |

(Continued)

OTHER PUBLICATIONS

PCT International Application No. PCT/US2020/018894, International Search Report and Written Opinion.

*Primary Examiner* — Darwin P Erezo
*Assistant Examiner* — Raihan R Khandker
(74) *Attorney, Agent, or Firm* — Phillips Winchester; Jared L. Cherry

(57) ABSTRACT

Disclosed herein are systems and methods for insertion tools for implanting electrode leads. In one embodiment, an insertion tool comprises a shaft having an outer cannula and an inner cannula. An actuator may be configured to transition the insertion tool between at least three configurations. In a first configuration, the inner cannula and the outer cannula are configured to receive the lead in the shaft. In a second configuration, the inner cannula and the outer cannula are configured to secure the lead in the shaft. In a third configuration, the inner cannula and the outer cannula are configured to cause the lead to separate from the insertion tool and implant in adjacent tissue.

12 Claims, 9 Drawing Sheets

(56) References Cited

U.S. PATENT DOCUMENTS

| | | | |
|---|---|---|---|
| 2003/0212446 A1 | 11/2003 | Kaplan | |
| 2004/0153098 A1 | 8/2004 | Chin | |
| 2005/0004644 A1 | 1/2005 | Kelsch | |
| 2011/0160824 A1* | 6/2011 | Ware | H01R 24/58 607/116 |
| 2011/0319909 A1* | 12/2011 | Thenuwara | A61B 17/3468 606/129 |
| 2012/0010627 A1* | 1/2012 | Watschke | A61M 25/01 606/129 |
| 2012/0232552 A1* | 9/2012 | Morgenstern Lopez | A61B 5/24 606/45 |
| 2014/0276927 A1* | 9/2014 | Barker | A61N 1/05 606/129 |
| 2015/0005857 A1* | 1/2015 | Kern | A61N 1/05 607/116 |
| 2015/0073431 A1* | 3/2015 | Barker | A61M 25/06 606/129 |
| 2015/0342670 A1 | 12/2015 | Pellegrino et al. | |
| 2016/0367820 A1* | 12/2016 | Torres Morales | A61N 1/3752 |
| 2017/0259039 A1* | 9/2017 | Gordon | A61M 25/0194 |
| 2018/0104481 A1* | 4/2018 | Boggs | A61B 17/3468 |
| 2018/0333173 A1* | 11/2018 | Wang | A61N 1/056 |
| 2019/0038443 A1* | 2/2019 | Sicotte | A61F 2/962 |
| 2019/0223768 A1* | 7/2019 | Muller | A61B 17/3421 |

* cited by examiner

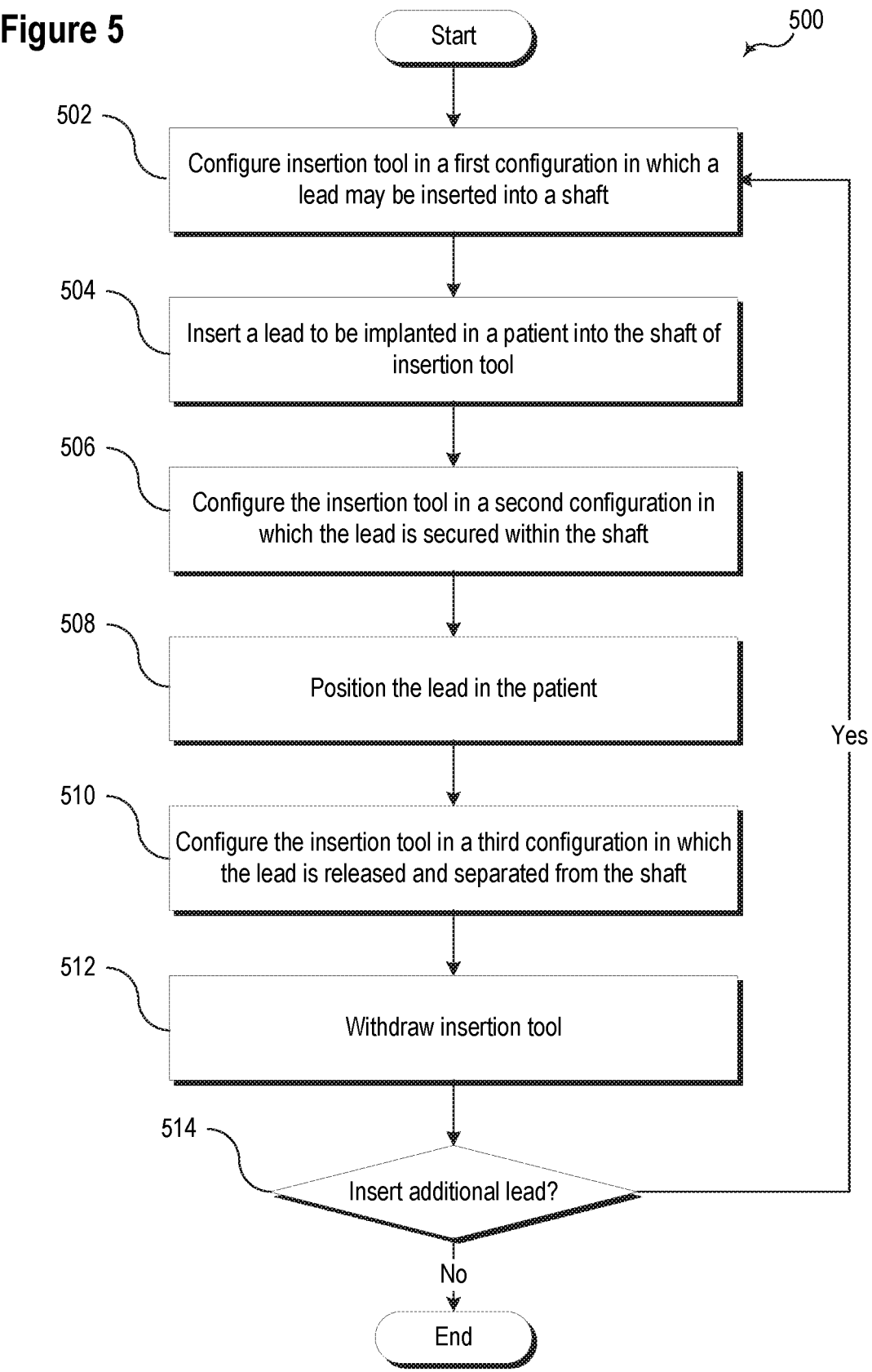

SYSTEMS AND METHODS FOR IMPLANTING ELECTRODE LEADS

FEDERALLY SPONSORED RESEARCH OR DEVELOPMENT

This invention was made with U.S. Government support under one or more of contract no. U44NS067784 awarded by National Institutes of Health and contract no. HR0011-15-C-0036 awarded by Defense Advanced Research Projects Agency. The U.S. Government may have certain rights in this invention.

TECHNICAL FIELD

This disclosure relates to systems and methods for implanting electrodes. More particularly, but not exclusively, such systems and methods may be utilized to implant a plurality of electrodes coupled to a common housing.

BRIEF DESCRIPTION OF THE DRAWINGS

FIG. 5 illustrates a flow chart of a method for inserting an electrode using an insertion tool consistent with embodiments of the present disclosure.

DETAILED DESCRIPTION OF PREFERRED EMBODIMENTS

Figure 1:
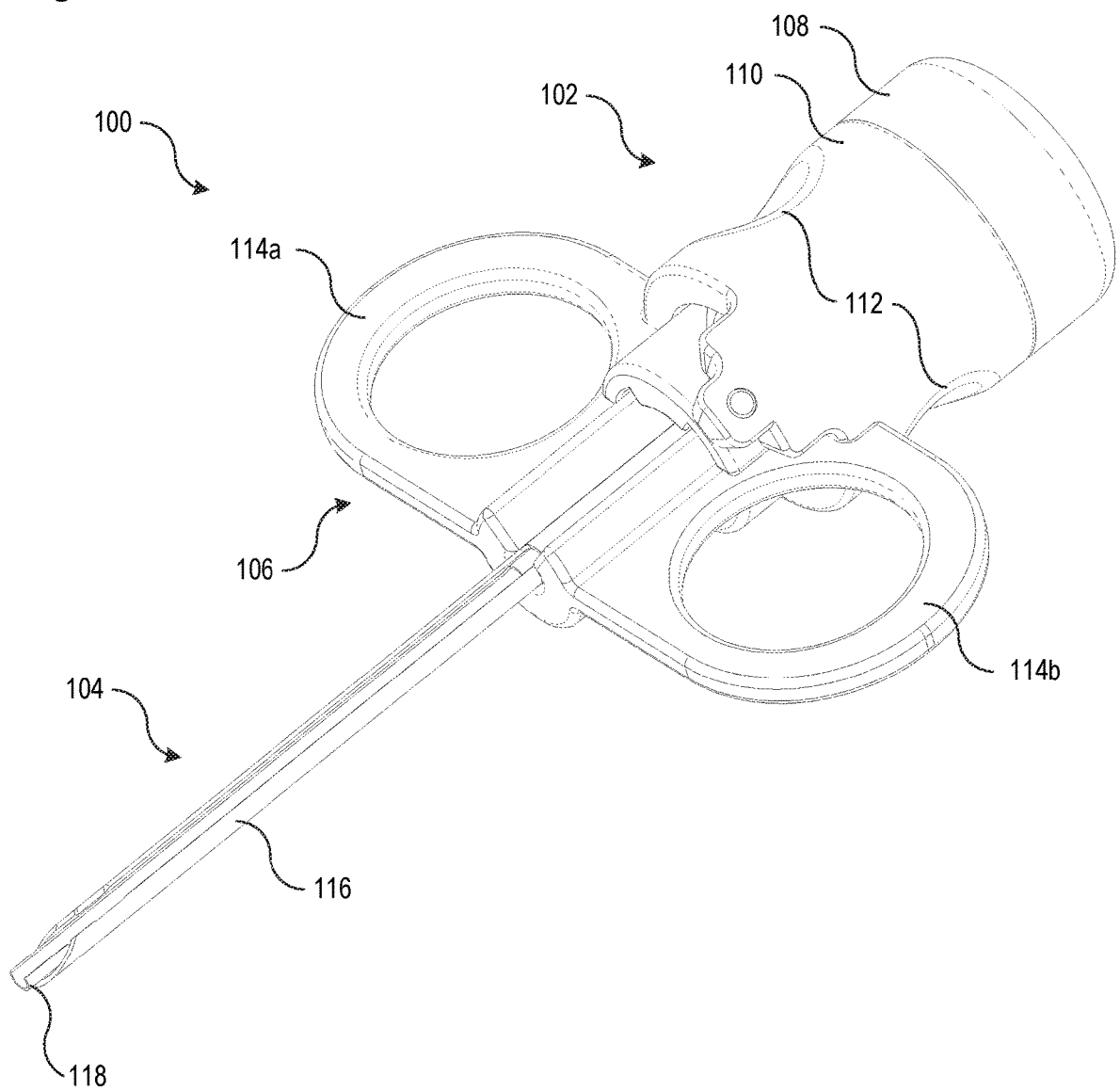
FIG. 1 illustrates a perspective view of an insertion tool for implanting electrodes consistent with embodiments of the present disclosure.

Disclosed herein are systems and methods for implanting electrodes that may be utilized in a variety of applications. In certain embodiments, the electrode insertion tool may be used to insert an array of electrodes on a plurality of leads coupled to a single housing. Such an electrode array may be utilized to control prosthetic devices or to perform other functions. A prosthetic device may be controlled using existing muscle groups in the residual limb that the user may be able to voluntarily activate. By connecting sensors to these muscles, the patient may be able to control the prosthetic device by activating the remaining muscles. The sensors may be connected to amplification and acquisition circuitry and a processor to control movement in a prosthetic device. As used in the present disclosure, the term myoelectric prosthesis refers to devices that use biopotential signals or potentials from voluntarily activated muscles to control the movements of a prosthesis.

In connection with a myoelectric prosthesis, biopotential signals may be collected via an electrode, lead, or sensor. Leads are structures that contain one or more electrodes or sensors that are individually placed, or placed in conjunction with other leads. Biopotential channels are electrical differences recorded between one or more electrodes. Electrodes/leads/sensors may be placed on or near the surface of the muscle or implanted into the muscle. A biopotential-signal-receiving device may also be implanted and may connect with an external transceiver via a wireless communication channel.

The insertion tool disclosed herein may be used during a surgical procedure to implant an electrode having a plurality of leads. Each lead may be separately positioned within a muscle group, and thus may help to provide broad coverage of the biopotential signals in the implant area. A lead to be implanted may be loaded into a shaft when the insertion tool is in a first configuration. The lead may be secured in the shaft and positioned within a patient while the insertion tool is in a second configuration. The lead may be released from the shaft and separated from the insertion tool while the insertion tool is in a third configuration.

In various embodiments, the shaft may include an inner cannula and an outer cannula that may be rotated and translated with respect to one another. In one specific embodiment, each of the first cannula and the second cannula may have a substantially C-shape in cross section. The first position may correspond to a rotational configuration of the first cannula and the second cannula in which the open portion of the C-shaped first and second cannula are aligned, such that the lead may be inserted. The second position may correspond to a rotational configuration of the first cannula and the second cannula in which the open portion of the first cannula is closed, either partially or completely, by the second cannula. The third position may cause the open portions of the first cannula and second cannula to align, such that the lead may exit from the shaft. Further, in the third position, the second cannula may move along a common axis with the first cannula. The movement of the second cannula with respect to the first cannula may facilitate or cause the separation of the lead from the insertion tool.

FIG. 1 illustrates a perspective view of an insertion tool 100 for implanting electrodes consistent with embodiments of the present disclosure. Insertion tool 100 may include an actuator 102, a shaft 104, and a grasp 106. The actuator 102, which is described in greater detail in connection with FIGS. 2A-2H, allows insertion tool 100 to be configured in a plurality of positions to facilitate implantation of a lead. A plurality of indentions 112 are disposed on opposite sides of a cover 110 and may facilitate rotation of cover 110 by providing finger grips.

Shaft 104 comprises an outer cannula 116 and an inner cannula 118, each of which has a cross section that is substantially C-shaped. The outer cannula 116 and the inner cannula 118 are disposed about a central axis. The inner cannula 118 may be rotated and moved with respect to the outer cannula 116 to receive the lead, secure the lead for positioning in the patient, and to separate the lead from the insertion tool 100. The rotation and movement of the inner cannula 118 with respect to the outer cannula 116 may be performed using the actuator 102.

In the illustrated embodiment, the inner cannula 118 may extend beyond the end of the outer cannula 116. In one specific embodiment, the inner cannula 118 may extend a maximum of 5 millimeters beyond the outer cannula 116 in a configuration for separating a lead from the insertion tool 100. The extension of the inner cannula 118 beyond the outer cannula 116 may facilitate the separation of the lead from the shaft by pushing the lead further into surrounding tissue and then retracting.

Grasp 106 may be used by a user to create a compressive force to manipulate actuator 102. A user may insert fingers into finger loops 114a, 114b. The user's thumb may be disposed on spin cap 108. Spin cap 108 may be configured to rotate with respect to cover 110 and actuator 102. Spin cap 108 may allow the user's thumb to remain fixed on the spin cap 108 while the cover 110 and actuator rotate and/or translate outer cannula 116 and inner cannula 118.

Figure 2A:
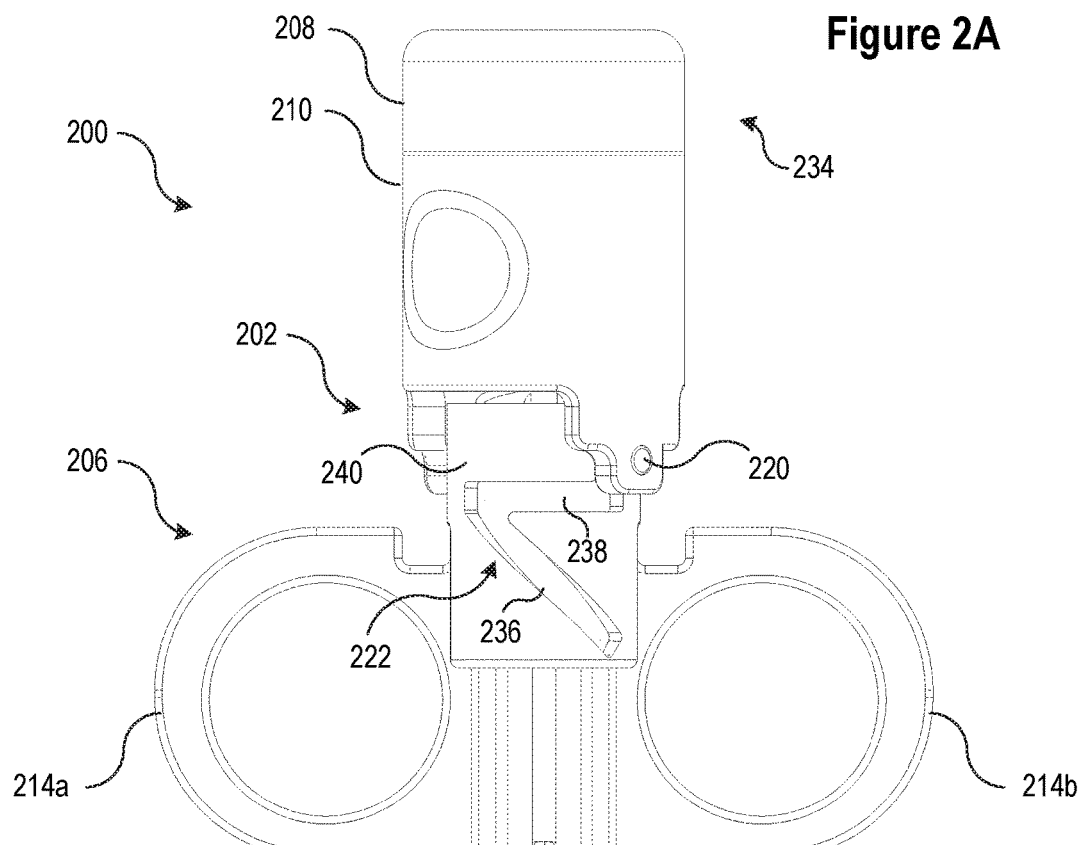
FIG. 2A illustrates a view of an insertion tool in a first position consistent with embodiments of the present disclosure.

FIG. 2A illustrates a view of an insertion tool 200 in a first position consistent with embodiments of the present disclosure. In the illustrated position, a lead (not shown) to be implanted may be introduced into shaft 204. A terminal end of the lead may be introduced near a distal end 232 of shaft 204. A fixed element 240 may comprise a channel 222 configured to receive a pin 220 coupled to a rotating cover 210. Channel 222 may comprise a horizontal portion 238 and a diagonal portion 236. Pin 220 may be moved through a horizontal portion 238 of channel 222 by rotating cover 210. As may be appreciated, rotating cover 210 may rotate with respect to fixed element 240 as pin 220 moves through channel 222.

The cover may be coupled to the inner cannula 218, and accordingly, rotation and/or movement of rotating cover 210 may cause rotation and/or movement of inner cannula 218. In the illustrated embodiment, movement of pin 220 through the horizontal portion 238 of channel 222 may allow inner cannula 218 to be rotated approximately 90 degrees with respect to outer cannula 216.

A grasp 206 may allow a user to exert a compressive force on insertion tool 200. In the illustrated embodiment, grasp 206 comprises finger loops 214a, 214b. In some embodiments, half-loops, quarter-loops, ridges, or a variety of other elements may be use to allow a user to generate a compressive force on insertion tool 200 using the user's fingers and thumb.

Figure 2B:
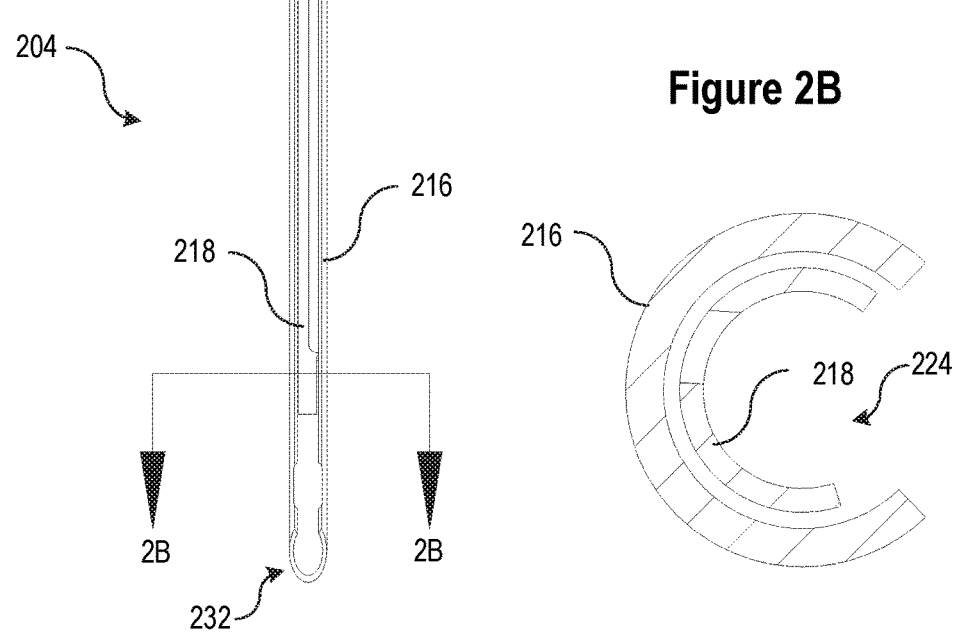
FIG. 2B illustrates an enlarged cross-sectional view taken along line 2B-2B in FIG. 2A and shows an outer cannula and an inner cannula in a rotational configuration to receive a lead to be implanted in a patient consistent with embodiments of the present disclosure.

FIG. 2B illustrates an enlarged cross-sectional view taken along line 2B-2B in FIG. 2A and shows an outer cannula 216 and an inner cannula 218 in a rotational configuration to receive a lead to be implanted in a patient consistent with embodiments of the present disclosure. Outer cannula 216 and inner cannula 218 are substantially C-shaped. In the illustrated rotational configuration, the open portions of each of the outer cannula 216 and the outer cannula 218 align to create an opening 224 into which the lead may be inserted.

Figure 2C:
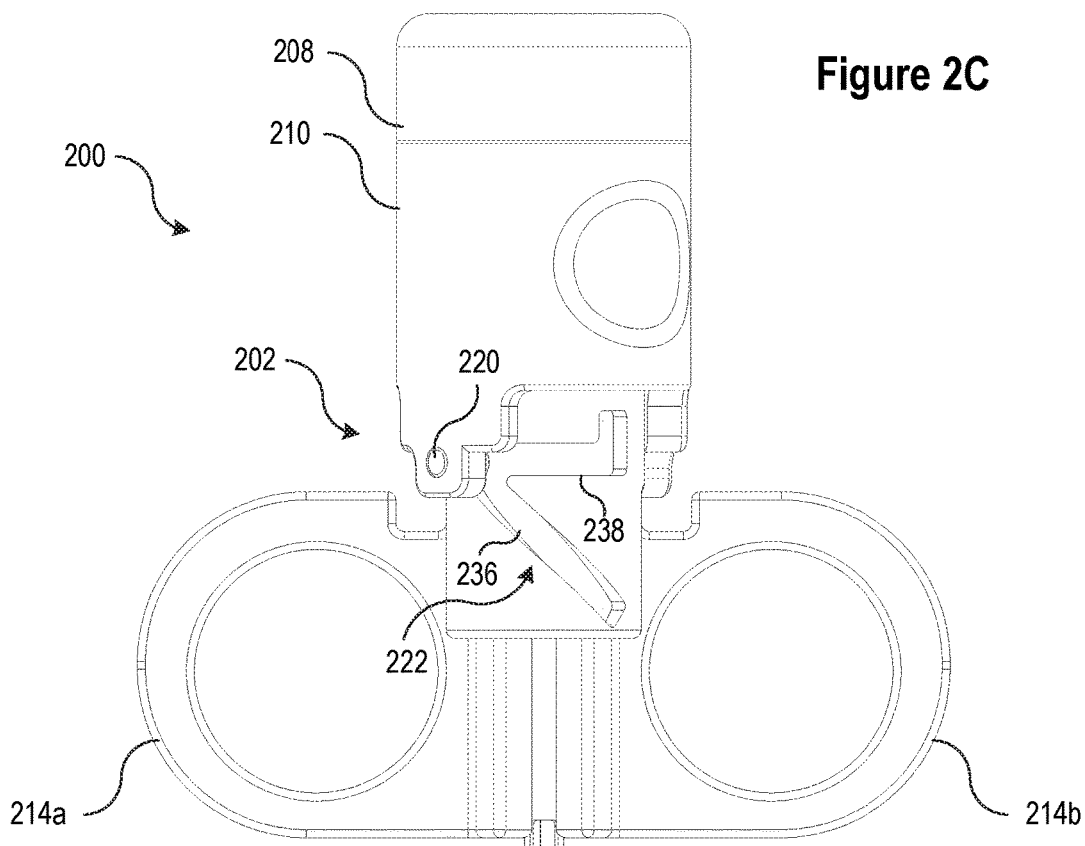
FIG. 2C illustrates a view of the insertion tool of FIG. 2A in a second position consistent with embodiments of the present disclosure.

FIG. 2C illustrates a view of the insertion tool of FIG. 2A in a second position consistent with embodiments of the present disclosure. A channel 222 may be configured to receive a pin 220 coupled to rotating cover 210. As may be appreciated by comparison of FIG. 2C and FIG. 2A, the rotating cover 210 has been rotated to the left within a horizontal portion 238 of channel 222. Pin 220 may travel along a horizontal portion 238 of channel 222 while rotating cover 210 is rotated. The cover may be coupled to the inner cannula 218. Movement of pin 220 through the horizontal portion 238 of channel 222 may allow inner cannula 218 to be rotated approximately 90 degrees with respect to outer cannula 216. Further, pin 220 may be moved along diagonal portion 236 of channel 222 by exerting a compressive force utilizing finger loops 214a, 214b and spin cap 208. Movement of pin 220 along diagonal portion 236 of channel 222 may cause rotation of the inner cannula 218 with respect to the outer cannula 216 and may also cause inner cannula 218 to move with respect to the outer cannula 216. In some embodiments, the movement of inner cannula 218 with respect to outer cannula 216 may cause inner cannula 218 to extend beyond outer cannula 216.

Figure 2D:
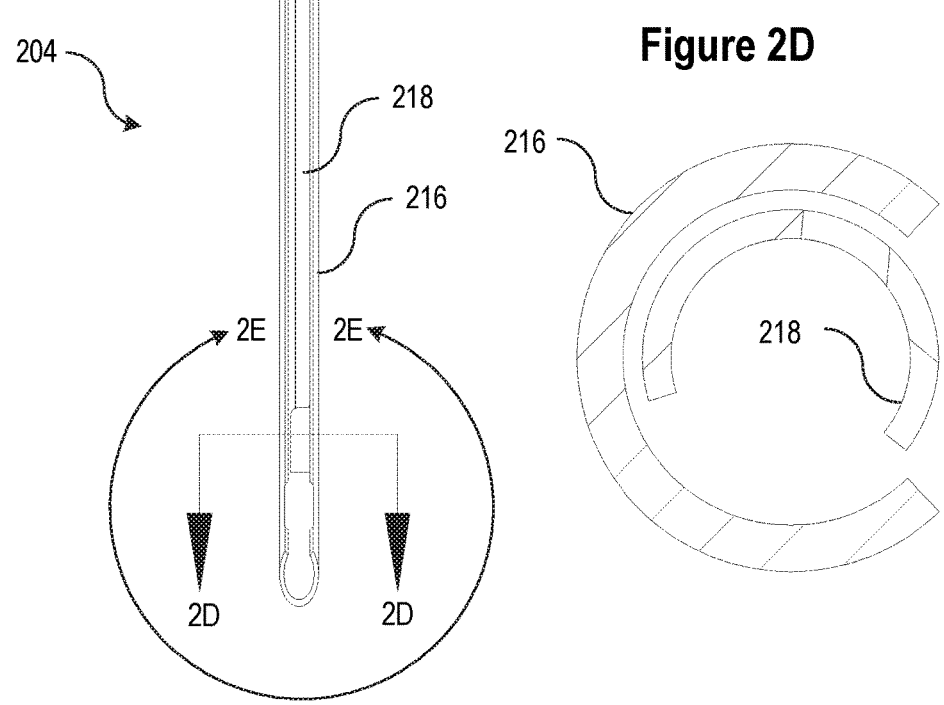
FIG. 2D illustrates an enlarged cross-sectional view taken along line 2D-2D in FIG. 2C and shows an outer cannula and an inner cannula in a rotational configuration to secure a lead to be implanted in a patient consistent with embodiments of the present disclosure.

FIG. 2D illustrates an enlarged cross-sectional view taken along line 2D-2D in FIG. 2C and shows an outer cannula 216 and an inner cannula 218 in a rotational configuration to secure a lead to be implanted in a patient consistent with embodiments of the present disclosure. As may be appreciated by comparison of FIG. 2B with FIG. 2D, inner cannula 218 has been rotated with respect to outer cannula 216. As a result, opening 224 shown in in FIG. 2B is closed in FIG. 2D. The configuration illustrated in FIG. 2D may secure a lead to be implanted in a patient by preventing the lead from exiting the shaft 216 while the lead is positioned in the patient.

Figure 2E:
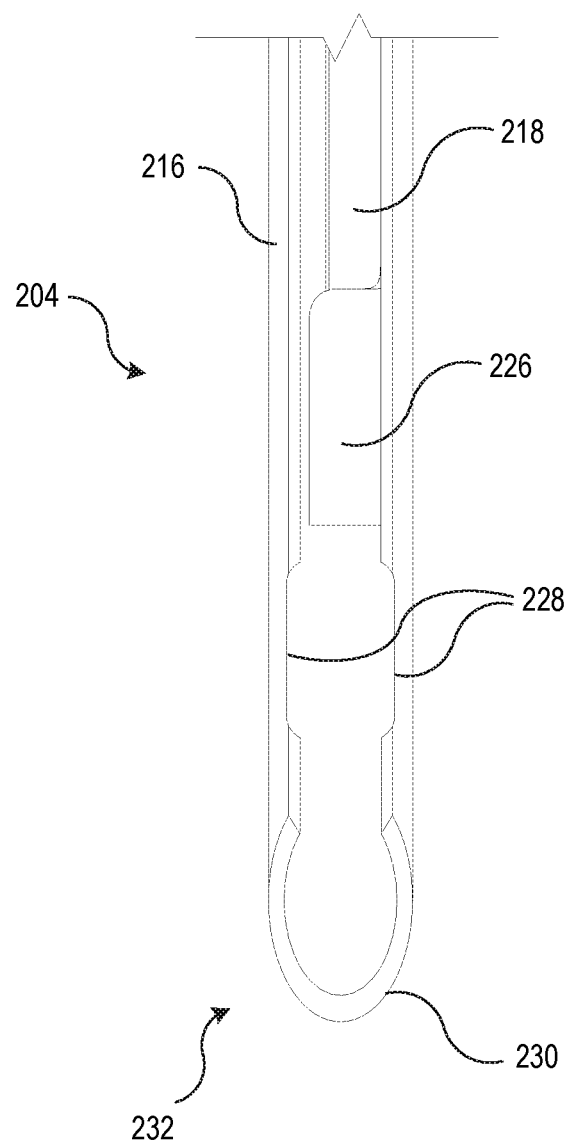
FIG. 2E illustrates an enlarged view of a distal end of the insertion tool of FIG. 2C consistent with embodiments of the present disclosure.

FIG. 2E illustrates an enlarged view of a distal end of insertion tool of FIG. 2C consistent with embodiments of the present disclosure. Inner cannula 218 may comprise a retention element 226 that extends across an opening in outer cannula 216 in the illustrated configuration. In the illustrated embodiment, retention element 226 is disposed at a distal end of inner cannula 218 and comprises a relatively small portion of inner cannula 218. As a result of the relatively small size of retention element 226 in comparison to inner cannula 218, outer cannula 216 and inner cannula 218 create an open channel along most of shaft 204 in the second position illustrated in FIG. 2C. As discussed in greater detail in connection with FIG. 4, the open channel along at least a portion of shaft 204 may facilitate implantation of a plurality of leads coupled to a single housing. Outer cannula 216 comprises a notch 228 near distal end 232. In some embodiments, a lead may comprise an anchor at a terminal end. Notch 228 may be configured to facilitate introduction of the anchor within shaft 204. A tip 230 disposed at distal end 232 may be sharpened to facilitate insertion of insertion tool 200 into tissue and placement of the lead in the tissue.

Figure 2F:
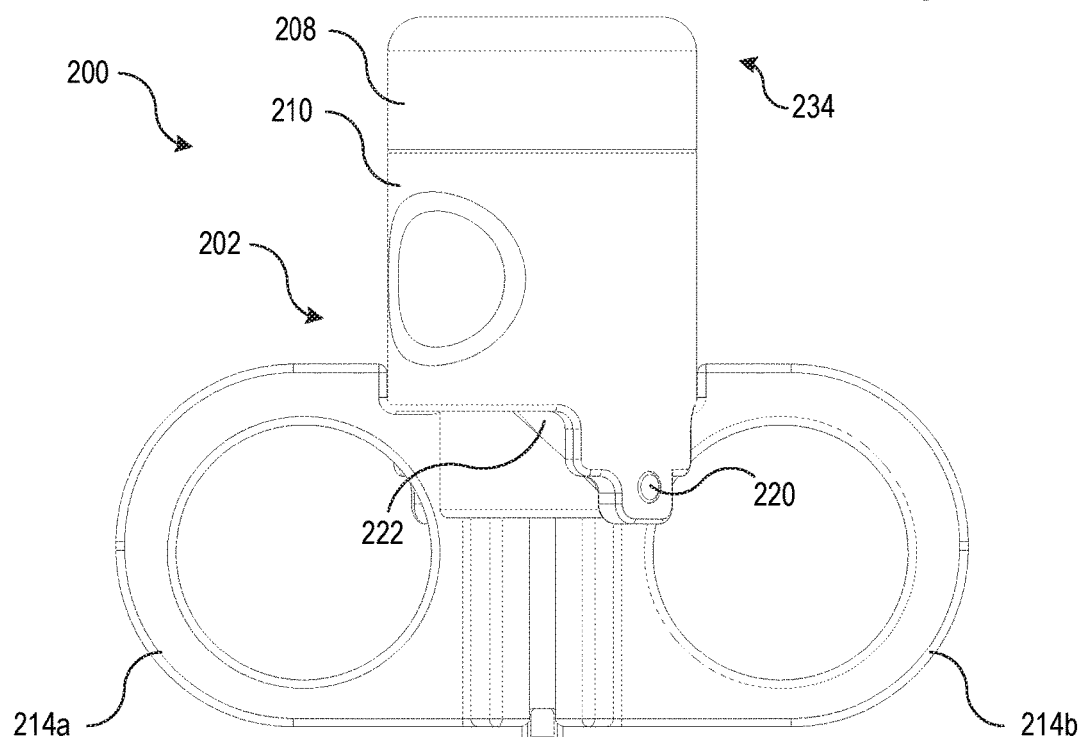
FIG. 2F illustrates a view of the insertion tool of FIG. 2A in a third position consistent with embodiments of the present disclosure.

FIG. 2F illustrates a view of the insertion tool of FIG. 2A in a third position consistent with embodiments of the present disclosure. As may be appreciated by comparing FIG. 2D to FIG. 2F, pin 220 has been moved along the diagonal portion of channel 222 by exerting a compressive force on insertion tool 200. The compressive force may cause pin 220 to transition from the horizontal portion 238 of the channel 220 to the diagonal portion 236. A user may exert a compressive force utilizing finger loops 214a, 214b and spin cap 208. The spin cap 208 may be disposed at a proximal end 234 with respect to a user of insertion tool 200. Movement of pin 220 along diagonal portion 236 of channel 222 may cause rotation of the inner cannula 218 with respect to the outer cannula 216 and may also cause inner cannula 218 to move with respect to the outer cannula 216.

As pin 220 travels through diagonal portion 236 of channel 222, inner cannula 218 may be both rotated and moved with respect to outer cannula 216. An operator of insertion tool 200 may exert compressive force once the lead is placed in a desired position. Further, the movement of the inner cannula 218 with respect to the outer cannula 216 may facilitate separation of the lead from the shaft 204. In various embodiments, the user may determine when the insertion tool 200 is configured in the third position because pin 220 reaches the end of channel 222.

Insertion tool 200 includes several features to facilitate implantation of a lead by an operator using a single hand. More specifically, spin cap 208 and finger loops 214a, 214b allow the user to generate a compressive force between the user's thumb and fingers. The free rotation of the spin cap 208 allows rotating cover 210 to rotate as pin 220 travels through diagonal portion 236 of channel 222 while the user exerts a compressive force with the user's thumb. As discussed below in connection with FIG. 2G, at the terminal end of channel 222, inner cannula 218 extends beyond outer cannula 218 to facilitate separation of the lead from insertion tool 200.

Figure 2G:
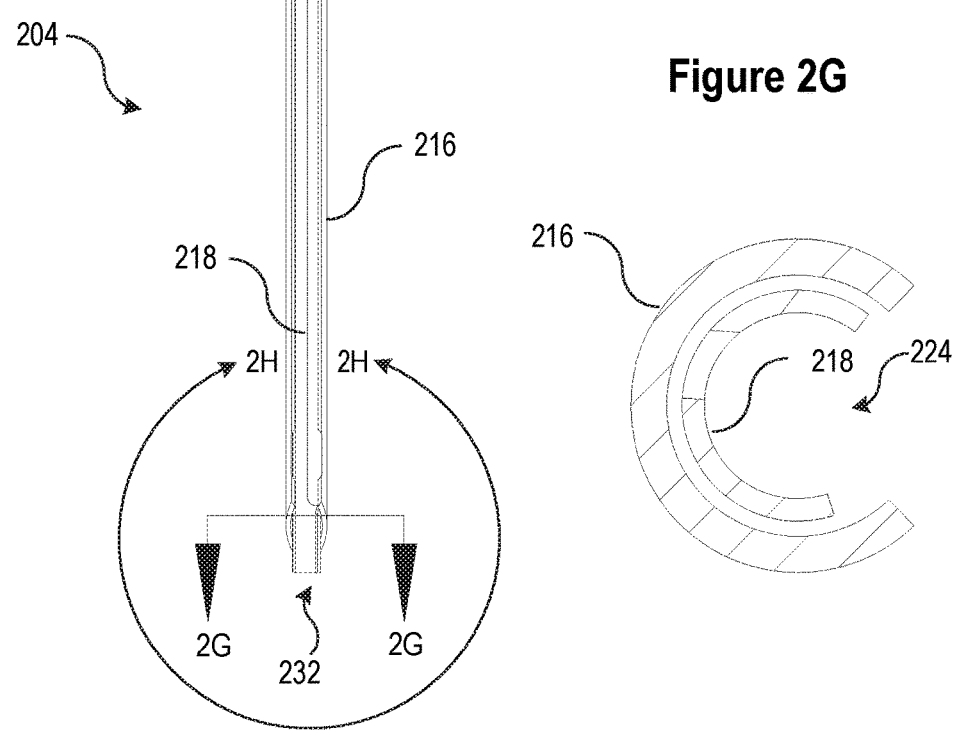
FIG. 2G illustrates an enlarged cross-sectional view taken along line 2G-2G in FIG. 2F and shows an outer cannula and an inner cannula in a rotational configuration to facilitate separation of the lead from the insertion tool consistent with embodiments of the present disclosure.

FIG. 2G illustrates an enlarged cross-sectional view taken along line 2G-2G in FIG. 2F and shows an outer cannula 216 and an inner cannula 218 in a rotational configuration to facilitate separation of the lead from insertion tool 200 consistent with embodiments of the present disclosure. As illustrated, the inner cannula 218 and the outer cannula 216 are in similar rotational position to that shown in FIG. 2B, such that an opening 224 exists. The lead may separate from the insertion tool 200 through opening 224.

Figure 2H:
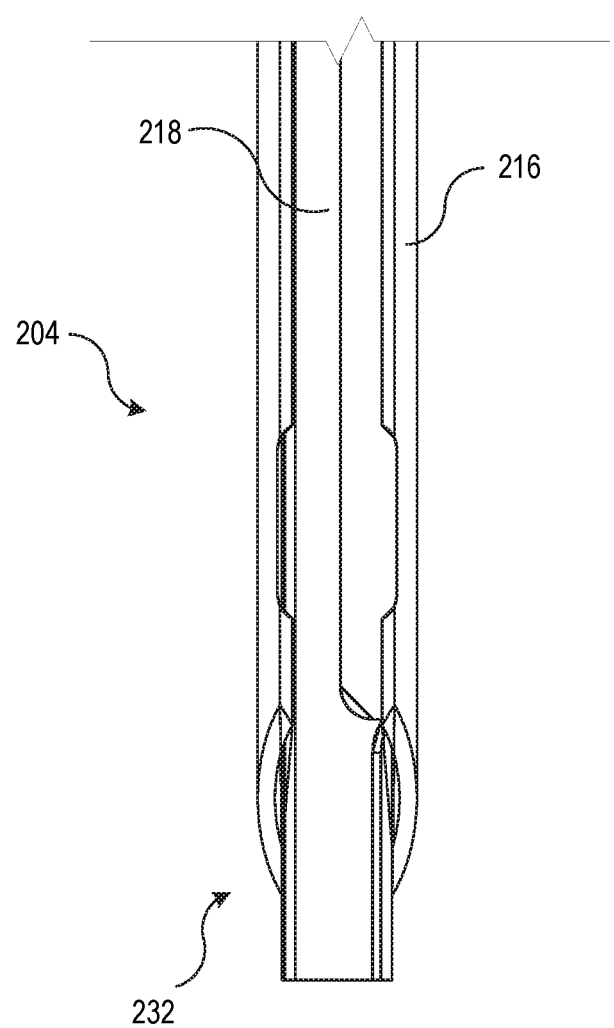
FIG. 2H illustrates an enlarged view of a distal end of the insertion tool of FIG. 2F consistent with embodiments of the present disclosure.

FIG. 2H illustrates an enlarged view of a distal end 232 of the insertion tool of FIG. 2F consistent with embodiments of the present disclosure. As illustrated in the third position shown in FIGS. 2F and 2G, the inner cannula 218 extends beyond the outer cannula 216. This configuration may facilitate separation of the lead from the insertion tool by pushing the lead beyond the distal end of the shaft 204. Moreover, in some embodiments, a lead may include an anchor disposed at a terminal end. The extension of the inner cannula 218 beyond the outer cannula 216 may help to set the anchor in surrounding issue. In one specific embodiment, the inner cannula 218 may be configured to extend a maximum distance of 5 millimeters beyond the outer cannula 216 in the third position.

Once insertion tool 200 is configured in the third position, the insertion tool 200 may be withdrawn. In some embodiments, a compressive force may be exerted using the spin cap and finger loops to transition insertion tool 200 from the second position to the third position. Insertion tool 200 may transition from the third position to the second position in the absence of compressive force. In various embodiments, a spring may be compressed as the insertion tool transitions from the second position to the third position. Decompression of the spring may cause rotation and translation of the inner cannula with respect to the outer cannula. The insertion tool may be returned to the default configuration, a new lead to be inserted may be placed in the shaft, and the new lead may be implanted using the same process described in connection with FIGS. 2A-2H.

Figure 3:
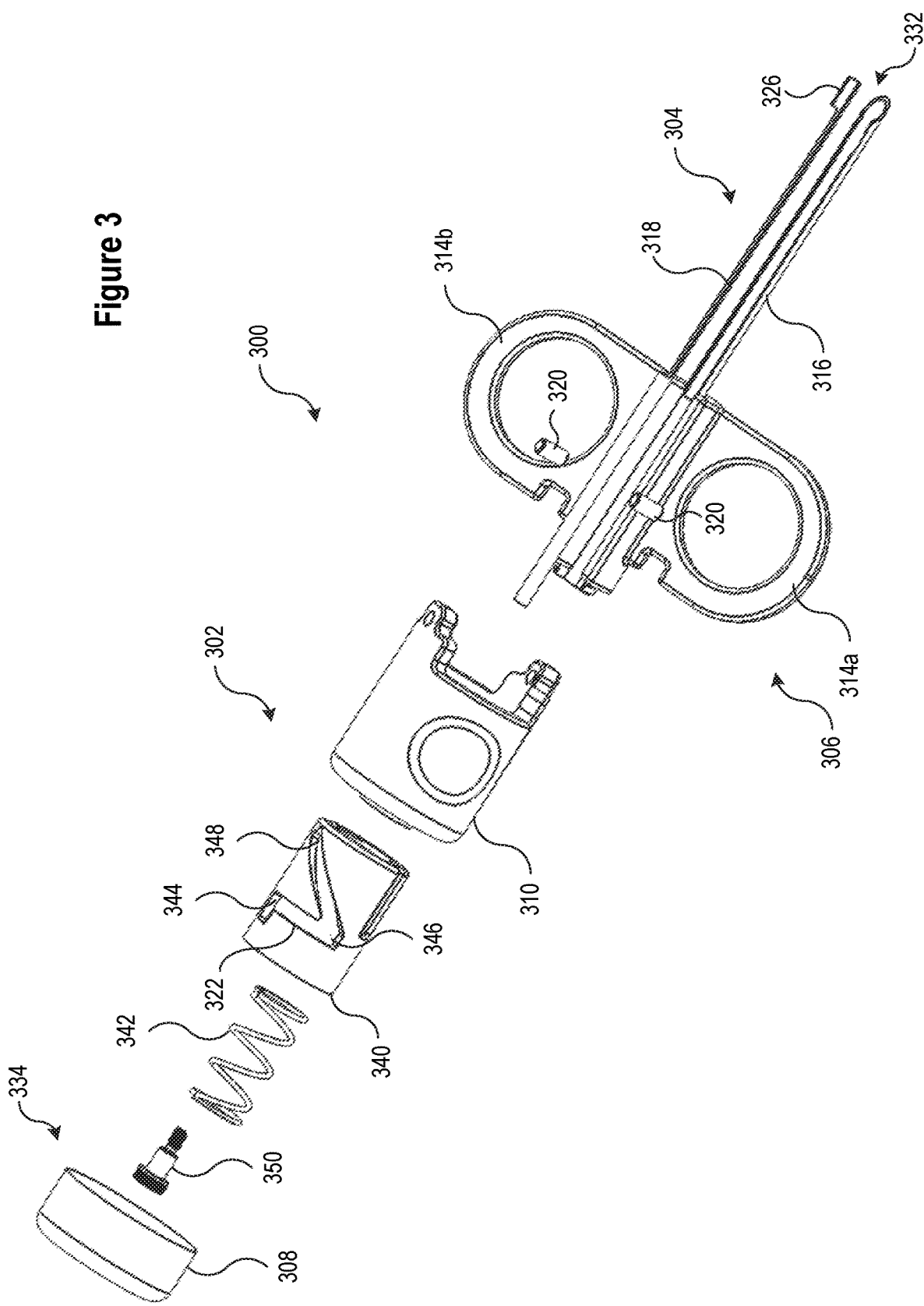
FIG. 3 illustrates an exploded view of an insertion tool 300 consistent with the present disclosure.

FIG. 3 illustrates an exploded view of an insertion tool 300 consistent with the present disclosure. Insertion tool 300 includes an actuator 302, a shaft 304, and a grasp 306. The actuator 302 allows insertion tool 300 to be configured in a plurality of positions to facilitate implantation of a lead. Shaft 304 comprises an outer cannula 316 and an inner cannula 318. Inner cannula 318 may include a retention element 326 disposed at a distal end 332. Inner cannula 318, including retention element 326, may rotate with respect to outer cannula 316. Retention element 326 may secure a lead to be implanted in the shaft 304 while the lead is positioned in a patient.

In the illustrated embodiment, actuator 302 may comprise fixed element 340, channel 322, rotating cover 310, and pin 320. The inner cannula 318 may be coupled to the rotating cover 310, and accordingly, may be translated and rotated with respect to the outer cannula 316. Actuator 302 may be actuated during implantation of a lead using insertion tool 300.

Insertion tool 300 may be configured in at least three positions by manipulation of actuator 302 that changes the rotation and translation of the inner cannula 318 with respect to the outer cannula 316. In a first position, pin 320 may be positioned at 344 in channel 322. In the first position, insertion tool 300 may be configured to receive a lead to be implanted. In a second position, pin 320 may be positioned at 346 in channel 322. In the second position, insertion tool 300 may be configured to secure a lead to be to be implanted within shaft 304. In a third position, pin 320 may be positioned at 348 in channel 322. In the third position, insertion tool 300 may be configured to release the lead from the shaft 304 and to separate the lead from the insertion tool 300.

Grasp 306 may be used to create a compressive force to manipulate actuator 302. The user's thumb may be disposed on spin cap 308. Spin cap 308 may be coupled to rotating cover 310 using a rotational coupling 350. A user may exert a force on spin cap 308 with the user's thumb while the user's fingers engage finger loops 314a, 314b. The compressive force may compress spring 342. When the compressive force is released, spring 342 may decompress. In various embodiments, decompression of spring 342 may cause insertion tool 300 to transition from the third position to the second position in the absence of a compressive force. In other words, insertion tool 300 may remain in the third configuration only while a user is exerting a compressive force on insertion tool 300.

Figure 4:
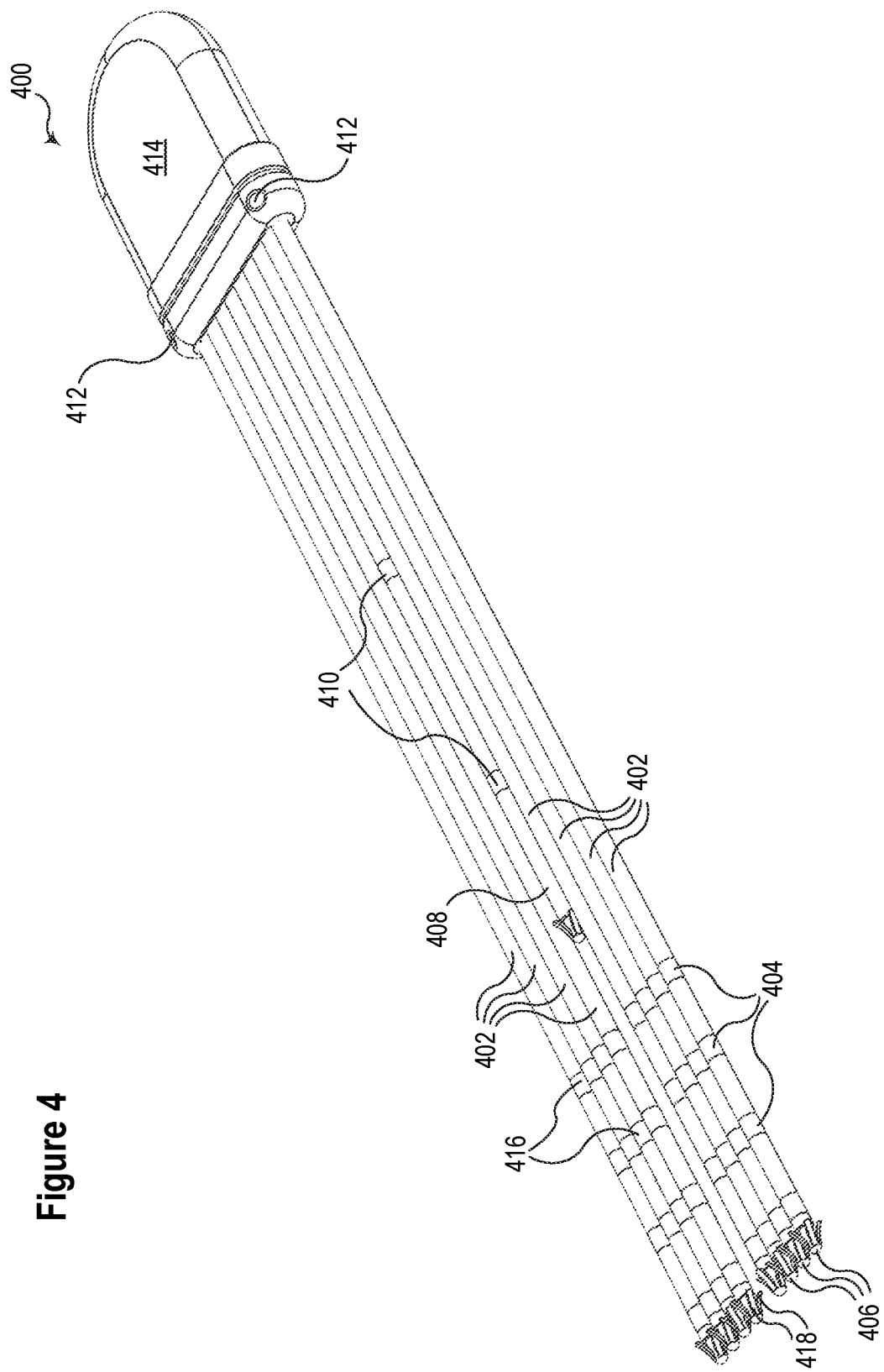
FIG. 4 illustrates one embodiment of an implantable component of a myoelectric sensor system having a plurality of leads and a plurality of electrodes disposed on each lead consistent with embodiments of the present disclosure.

FIG. 4 illustrates one embodiment of an implantable component 400 of a myoelectric sensor system having a plurality of leads 402 and a plurality of electrodes 404 disposed on each lead consistent with embodiments of the present disclosure. Various embodiments of the insertion tools disclosed in the present application may be used to implant the plurality of leads associated with implantable component 400. Additional information related to implantable component 400 is provided in U.S. patent application Ser. No. 15/870,362, filed on Jan. 12, 2018, and titled "Sensor System," which is incorporated in its entirety herein by reference.

The plurality of leads 402 may each connect to a hermetic feedthrough on a housing 414. In various embodiments, the housing 414 may be formed of a bio-compatible material and may be hermetically sealed to allow for implantation in a patient. In one specific embodiment, the housing 414 may be formed of ceramic. A plurality of suture holes 412 may be disposed on the housing 414 and may allow the housing to be secured to adjacent tissue. As discussed in greater detail below, the housing 414 may comprise electronics to receive signals from the plurality of electrodes 404 and to communicate with an associated device.

The plurality of leads 402 may be flexible and may be independently positioned within one or more muscle groups. The leads may be wire, helically wound wire, or of other constructions including a biostable polymer comprising a plurality of distinct conductive particles. In the illustrated embodiment, implantable component 400 includes eight full length leads 402, each of which includes four electrodes 404.

A reference lead 408 may include a plurality of reference electrodes 410. A reference electrode 410 may provide a stable electrical potential against which the electrical potential of other electrodes 404 may be amplified and acquired. The system may be referred to as a "single-ended" reference. The "single-ended" reference may allow for the generation of "virtual pairs" in digital signal processing, rather than using analog amplifiers.

In additional to creating differential pairs between reference electrodes 410 and electrodes 404, "virtual pairs" of electrodes may also be generated after acquisition by a comparison of the signal from any electrodes 404 to the signal from any other electrode. For example, a "virtual pair" may be created by comparison of the signals received by the two electrodes identified by reference number 416. In other words, a "virtual pair" may be generated as a difference between one of the plurality of electrodes and any other of the plurality of electrodes. A "virtual pair" may be generated from multiple signals from electrodes located on one lead or on separate leads. The ability to create a "virtual pair" based on two or more electrode signals provides a wide array of possible combinations. The large number of possible combinations may be analyzed to identify the specific combinations to achieve a specific result (e.g., utilization of a muscle group to control a prosthesis).

An anchor 406 may be disposed at the end of each lead 402 and reference lead 408. The anchors may be configured to hold the leads 402, 408 in place. In the illustrated embodiment, a plurality of flanges 418 may oppose motion in the direction of the housing 414. In contrast, when the leads 402, 408 are inserted, the flanges 418 may be pressed inward and offer little resistance. The plurality of flanges 418 may comprise an anchor 406 configured to secure the lead in tissue of a patient.

FIG. 5 illustrates a flow chart of a method 500 of implanting a plurality of electrodes using an insertion tool consistent with embodiments of the present disclosure. At 502, an insertion tool may be configured in a first configuration in which a lead may be inserted in a shaft. In one specific embodiment, the first configuration may correspond to the configuration of insertion tool 200 illustrated in FIG. 2A and FIG. 2B. At 504, a lead to be implanted may be inserted into the shaft of the insertion tool. In one specific embodiment, a lead to be implanted may correspond to one or more of the plurality of leads 402 illustrated in FIG. 4. At 506, the insertion tool may be configured in a second configuration in which the lead is secured in the shaft. In one specific embodiment, the second configuration may correspond to the configuration of insertion tool 200 illustrated in FIG. 2C, FIG. 2D, and FIG. 2E. At 508, the lead may be positioned in the patient. In certain embodiments, a plurality of leads comprising an electrode array may be implanted to ensure broad coverage in the implant area. At 510, the insertion tool may be configured in a third configuration in which the lead is released from the shaft and separated from the insertion tool. In one specific embodiment, the third configuration may correspond to the configuration of insertion tool 300 illustrated in FIG. 2F, FIG. 2G, and FIG. 2H. At 512, the insertion tool may be withdrawn, leaving the lead implanted in the patient. If additional leads remain to be inserted, at 514, method 500 may return to 502. Otherwise, method 500 may end.

Many changes may be made to the details of the above-described embodiments without departing from the underlying principles of the invention. The scope of the present invention should, therefore, be determined only by the following claims.

What is claimed is:

1. An insertion tool configured to implant a lead comprising an electrode in a patient, the insertion tool comprising:
   a shaft, comprising:
      an outer cannula, and
      an inner cannula at least partially disposed in the outer cannula along at least a portion of a length of the inner cannula;
   an actuator configured to configure the insertion tool in at least three configurations:
      a first configuration in which the inner cannula and the outer cannula are configured to receive the lead in the shaft;
      a second configuration in which the inner cannula and the outer cannula are configured to secure the lead in the shaft; and
      a third configuration in which the inner cannula and the outer cannula are configured to cause the lead to separate from the insertion tool and implant in adjacent tissue,
   wherein a compressive force exerted on the insertion tool causes the insertion tool to transition from the second configuration to the third configuration.

2. The insertion tool of claim 1, wherein the inner cannula and the outer cannula comprise a substantially C-shaped cross-section along at least a portion of their length.

3. The insertion tool of claim 1, wherein the actuator comprises a fixed element coupled to the outer cannula and a rotating element coupled to the inner cannula.

4. The insertion tool of claim 3, wherein the fixed element comprises a channel and the rotating element comprises a pin configured to engage with the channel.

5. The insertion tool of claim 4, wherein the channel comprises a first portion configured to cause rotation of the inner cannula with respect to the outer cannula in a first direction as the insertion tool transitions from the first configuration to the second configuration.

6. The insertion tool of claim 5, wherein the channel comprises a second portion configured to cause rotation of the inner cannula with respect to the outer cannula in a second direction as the insertion tool transitions from the second configuration to the third configuration.

7. The insertion tool of claim 1, further comprising a spring configured to be compressed by the compressive force, and further configured to cause the insertion tool to transition from the third configuration to the second configuration in the absence of the compressive force.

8. The insertion tool of claim 1, further comprising:
   a spin cap; and
   a grasp;
   wherein the grasp and the spin cap are configured to enable a user to exert the compressive force using a single hand.

9. The insertion tool of claim 1, wherein the inner cannula rotates and translates with respect to the outer cannula as the insertion tool transitions from the second configuration to the third configuration.

10. The insertion tool of claim 1, wherein the inner cannula extends beyond the outer cannula to deploy the lead.

11. The insertion tool of claim 8, wherein the grasp comprises a pair of finger loops.

12. An insertion tool configured to implant a lead comprising an electrode in a patient, the insertion tool comprising:
- a spin cap comprising a first surface configured to contact a hand of a user;
- a grasp comprising a second surface configured to contact at least one of the user's fingers on the hand;
- a shaft, comprising:
  - an outer cannula, and
  - an inner cannula at least partially disposed in the outer cannula along at least a portion of a length of the inner cannula;
- an actuator configured to configure the insertion tool in at least three configurations:
  - a first configuration in which the inner cannula and the outer cannula are configured to receive the lead in the shaft;
  - a second configuration in which the inner cannula and the outer cannula are configured to secure the lead in the shaft;
  - a third configuration in which the inner cannula and the outer cannula are configured to cause the lead to separate from the insertion tool and implant in adjacent tissue;
- wherein a compressive force between the spin cap and the grasp causes the insertion tool to transition from the second configuration to the third configuration and the grasp and the spin cap are configured to enable a user to exert the compressive force using a single hand.

* * * * *